United States Patent
Hourigan et al.

(10) Patent No.: US 9,155,693 B2
(45) Date of Patent: Oct. 13, 2015

(54) SOLUBILIZED MAGNOLOL ANALOGS

(75) Inventors: Regina Hourigan, Metuchen, NJ (US);
Jeffrey Mastrull, Flemington, NJ (US);
Jairajh Mattai, Piscataway, NJ (US);
James Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/362,892

(22) PCT Filed: Dec. 15, 2011

(86) PCT No.: PCT/US2011/065020
§ 371 (c)(1),
(2), (4) Date: Jun. 4, 2014

(87) PCT Pub. No.: WO2013/089718
PCT Pub. Date: Jun. 20, 2013

(65) Prior Publication Data
US 2014/0348761 A1    Nov. 27, 2014

(51) Int. Cl.
*A61K 36/575* (2006.01)
*A61Q 11/00* (2006.01)
*A61Q 19/00* (2006.01)
*A61K 8/86* (2006.01)
*A61K 8/34* (2006.01)
*A61K 8/39* (2006.01)
*A61Q 19/10* (2006.01)
*A61K 8/21* (2006.01)
*A61K 8/25* (2006.01)
*A61K 8/29* (2006.01)
*A61K 8/41* (2006.01)
*A61K 8/46* (2006.01)
*A61K 8/60* (2006.01)
*A61K 8/84* (2006.01)

(52) U.S. Cl.
CPC ... *A61K 8/86* (2013.01); *A61K 8/21* (2013.01);
*A61K 8/25* (2013.01); *A61K 8/29* (2013.01);
*A61K 8/347* (2013.01); *A61K 8/39* (2013.01);
*A61K 8/416* (2013.01); *A61K 8/463* (2013.01);
*A61K 8/602* (2013.01); *A61K 8/84* (2013.01);
*A61K 36/575* (2013.01); *A61Q 11/00* (2013.01); *A61Q 19/10* (2013.01); *A61K 2800/10* (2013.01); *A61K 2800/49* (2013.01); *A61K 2800/74* (2013.01)

(58) Field of Classification Search
CPC ...... A61K 36/575; A61Q 11/00; A61Q 19/00
USPC .............................................. 424/49, 58, 401
See application file for complete search history.

(56) References Cited

U.S. PATENT DOCUMENTS

| | | | |
|---|---|---|---|
| 2005/0271609 A1* | 12/2005 | Fei et al. | 424/65 |
| 2006/0188551 A1 | 8/2006 | Hauser et al. | |
| 2007/0196296 A1* | 8/2007 | Osborne et al. | 424/61 |
| 2008/0274068 A1* | 11/2008 | Tanaka et al. | 424/60 |
| 2011/0281810 A1* | 11/2011 | Petersen et al. | 514/29 |
| 2012/0294812 A1* | 11/2012 | Fei et al. | 424/49 |
| 2012/0308489 A1* | 12/2012 | Yang et al. | 424/49 |

FOREIGN PATENT DOCUMENTS

| | | |
|---|---|---|
| CN | 1441664 A | 9/2003 |
| CN | 101321513 A | 12/2008 |
| CN | 101321560 A | 12/2008 |
| CN | 101460134 A | 6/2009 |
| JP | 07033624 A * | 2/1995 |
| WO | WO 2004062702 | 7/2004 |
| WO | WO 2011106003 | 9/2011 |
| WO | WO 2011106492 | 9/2011 |
| WO | WO 2011106493 | 9/2011 |

OTHER PUBLICATIONS

International Search Report and the Written Opinion issued in International Application PCT/US11/65020 mailed Oct. 31, 2012. WO.

* cited by examiner

*Primary Examiner* — Frederick Krass
*Assistant Examiner* — Tracy Liu

(57) ABSTRACT

A composition comprising a solubilized magnolol analog comprising at least one magnolol analog chosen from propyl magnolol, isopropyl magnolol, butyl magnolol, and isobutyl magnolol, and PPG-1-PEG-9 lauryl glycol ether. These solubilized analogs are useful in personal care, oral care, and home care compositions to provide anti-bacterial activity and reducing the expression of pro-inflammatory mediators.

12 Claims, No Drawings

SOLUBILIZED MAGNOLOL ANALOGS

CROSS-REFERENCE TO RELATED PATENT APPLICATIONS

The present application is a U.S. national stage entry under 35 U.S.C. §371 of Patent Cooperation Treaty Patent Application No. PCT/US2011/65020, filed Dec. 15, 2011, the entirety of which is incorporated herein by reference.

FIELD OF THE INVENTION

Disclosed are solubilized magnolol analogs.

BACKGROUND OF THE INVENTION

Magnolol analogs, such a propyl magnolol, isopropyl magnolol, butyl magnolol, and isobutyl magnolol, are known to have anti-bacterial activities and they are also shown to be capable of reducing the expression of pro-inflammatory mediators in oral tissues. The problem with using these magnolol analogs is their solubility in typical personal care, oral care, or home care compositions. Their use has been limited by their solubility. It would be desirable to solubilize these analogs to increase their use in personal, oral, or home care compositions. The problem is finding materials that can solubilize these analogs. Even in a given class of material, not all members of the class are effective at solubilizing these analogs.

BRIEF SUMMARY OF THE INVENTION

A composition comprising a solubilized magnolol analog comprising at least one magnolol analog chosen from propyl magnolol, isopropyl magnolol, butyl magnolol, and isobutyl magnolol, and PPG-1-PEG-9 lauryl glycol ether. Optionally, the composition can further include coceth-7 and PEG-40 hydrogenated castor oil.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

Disclosed is a composition comprising a solubilized magnolol analog comprising at least one magnolol analog chosen from propyl magnolol, isopropyl magnolol, butyl magnolol, and isobutyl magnolol, and PPG-1-PEG-9 lauryl glycol ether.

Propyl magnolol is 5,5'-di-n-propylbiphenyl-2,2'-diol, butyl magnolol is 5,5'-di-n-butylbiphenyl-2,2'-diol, isopropyl magnolol is 5,5'-di-isopropylbiphenyl-2,2'-diol, and isobutyl magnolol is 5,5'-di-isobutylbiphenyl-2,2'-diol.

The PPG-1-PEG-9 lauryl glycol ether is capable of solubilizing up to 100 g per liter of neat propyl magnolol or isopropyl magnolol or up to 50 g per liter of butyl magnolol or isobutyl magnolol. In certain embodiments, the amount of PPG-1-PEG-9 lauryl glycol ether is at least 10 times the weight of the propyl magnolol or isopropyl magnolol in the composition. In certain embodiments, the amount of PPG-1-PEG-9 lauryl glycol ether is at least 20 times the weight of butyl or isobutyl magnolol in the composition.

PPG-1-PEG-9 lauryl glycol ether is available as Eumulgin™ L from Cognis Corporation.

The PPG-1-PEG-9 lauryl glycol ether can also be included in combination with coceth-7 and PEG-40 hydrogenated castor oil. This combination is available as Eumulgin™ HPS from Cognis Corporation. When this combination is used, the solubility stays the same except for butyl magnolol. This combination solubilizes up to 100 g per liter of butyl magnolol as compared to up to 50 g per liter for PPG-1-PEG-9 lauryl glycol ether alone. In certain embodiments, the amount of this combination is at least 10 times the weight of butyl magnolol.

It was surprising that these two materials were capable of solubilizing the analogs. Many other solubilizers, such as PEG-7 glyceryl cocoate, poloxamer 124, PPG-2 hydroxyethyl cocoamide, PPG-5 laureth-5 (Eumulgin™ ES), PEG-8/SMDI copolymer, isopropyl myristate, or C12-15 alkyl benzoate are not able to solubilize isobutyl magnolol.

The amount of magnolol analog in the composition can be any desired amount. In certain embodiments, the amount is 0.01 to 5% by weight of the composition. In other embodiments, the amount is at least 0.05, at least 0.1, at least 0.2, at least 0.3, at least 0.4, at least 0.5, or at least 1% by weight up to 5% by weight of the composition. In other embodiments, the amount is any of the foregoing minimum amounts up to 4, up to 3, up to 2, or up to 1% by weight of the composition. The weight of the PPG-1-PEG-9 lauryl glycol or the PPG-1-PEG-9 lauryl glycol ether, coceth-7 and PEG-40 hydrogenated castor oil combination is then the amount to solubilize the analog with the minimum amount of the PPG-1-PEG-9 lauryl glycol or the PPG-1-PEG-9 lauryl glycol ether, coceth-7 and PEG-40 hydrogenated castor oil combination being based on the maximum solubility of the analog in the PPG-1-PEG-9 lauryl glycol or the PPG-1-PEG-9 lauryl glycol ether, coceth-7 and PEG-40 hydrogenated castor oil combination. In certain embodiments, the amount of the magnolol analog is 0.1, 0.2, 0.3, 0.4, or 0.5% by weight.

These solubilized analogs are useful in personal care, oral care, and home care compositions. Examples of personal care compositions include, but are not limited to, body wash/shower gel, liquid hand cleanser, bar soap, shampoo, conditioner, antiperspirant/deodorants, and cosmetics. Examples of oral care compositions include, but are not limited to, dentifrices, toothpastes, tooth powders, prophylaxis pastes, mouth rinses, lozenges, gums, gels, paints, confectionaries, and denture cleaners. Examples of oral care compositions that can include solubilized magnolol analogs can be found in WO2011/106492. Examples of home care compositions include, but are not limited to, dish liquids, dish pastes, hard surface cleaners, fabric conditioners, and laundry detergents.

In certain embodiments, the magnolol analog can be present in a body wash/shower gel, liquid hand cleanser, or shampoo in which each of these compositions include a surfactant. The magnolol analog can also be included in a soap (fatty acid soap), which can be in the shape of a bar soap.

EXAMPLES

The following are non-limiting prophetic examples of compositions that can include solubilized magnolol analogs.

| Liquid Cleanser (Body Wash or Liquid Hand Soap) | | |
|---|---|---|
| Ingredient Name | % Wt. Range | % Wt. Range |
| Propyl magnolol, isopropyl magnolol, or butyl magnolol | 0.01-1 | 0 |
| Isobutyl magnolol | 0 | 0.01-1% |
| PPG-1-PEG-9 lauryl glycol ether | At least 10 times the weight of the magnolol analog | At least 20 times the weight of the magnolol analog |
| Polyquaternium-7 | 0-0.25 | 0-0.25 |
| SO$_3$Na Pareth 145-2EO Sulfate | 8-12 | 8-12 |
| Cocamidopropyl Betaine | 2.5-7 | 2.5-7 |
| Decyl Glucoside | 0-2 | 0-2 |
| Demineralized Water and minors | Q.S. | Q.S. |
| Total Materials | 100 | 100 |

| Bar Soap | | |
|---|---|---|
| Ingredient Name | % Wt. Range | % Wt. Range |
| Propyl magnolol, isopropyl magnolol, or butyl magnolol | 0.01-1 | 0 |
| Isobutyl magnolol | 0 | 0.01-1% |
| PPG-1-PEG-9 lauryl glycol ether | At least 10 times the weight of the magnolol analog | At least 20 times the weight of the magnolol analog |
| Fatty acid soap | 75-85 | 75-85 |
| Demineralized Water and minors | Q.S. | Q.S. |
| Total Materials | 100 | 100 |

| Oral Care Composition | | |
|---|---|---|
| Ingredient | Weight % | Weight % |
| Purified water | Q.S. | Q.S. |
| Sorbitol | 19.45 | 19.45 |
| Glycerin | 20 | 20 |
| Sodium CMC-12 type USP | 1.1 | 1.1 |
| Iota carrageenan (LB 9505) | 0.4 | 0.4 |
| Sodium saccharin-USP | 0.3 | 0.3 |
| Sodium fluoride | 0.24 | 0.24 |
| Zeodent-115-dental type silica abrasive | 8.5 | 8.5 |
| Zeodent-165-synthetic amorphous PPT silica | 3 | 3 |
| Dental type silica sylodent XWA650 | 10 | 10 |
| Titannium dioxide (TiO2) | 0.5 | 0.5 |
| Sodium lauryl sulphate powder-NF | 1.5 | 1.5 |
| Flavor | 1 | 1 |
| Propyl magnolol, isopropyl magnolol, or butyl magnolol | 0.01-1 | 0 |
| Isobutyl magnolol | 0 | 0.01-1% |
| PPG-1-PEG-9 lauryl glycol ether | At least 10 times the weight of the magnolol analog | At least 20 times the weight of the magnolol analog |
| Total | 100 | 100 |

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A composition comprising a solubilized magnolol analog comprising:
   at least one magnolol analog chosen from propyl magnolol, isopropyl magnolol, butyl magnolol, and isobutyl magnolol, and
   PPG-1-PEG-9 lauryl glycol ether; and
   wherein the PPG-1-PEG-9 lauryl glycol ether is present in an amount of at least 10 times the weight of propyl magnolol or isopropyl magnolol or at least 20 times the weight of butyl magnolol or isobutyl magnolol.

2. The composition of claim 1, wherein the magnolol analog is present in an amount of 0.01 to 5% by weight of the composition.

3. The composition of claim 1 further comprising coceth-7 and PEG-40 hydrogenated castor oil.

4. The composition of claim 1 further comprising a surfactant.

5. The composition of claim 1 further comprising soap.

6. The composition of claim 5 in the form of a bar soap.

7. The composition of claim 4 in the form of a liquid cleanser.

8. The composition of claim 1 in the form of an oral care composition.

9. The composition of claim 1, wherein magnolol analog is propyl magnolol.

10. The composition of claim 1, wherein magnolol analog is isopropyl magnolol.

11. The composition of claim 1, wherein magnolol analog is butyl magnolol.

12. The composition of claim 1, wherein magnolol analog is isobutyl magnolol.

* * * * *